(12) United States Patent
Nebel et al.

(10) Patent No.: US 10,921,235 B2
(45) Date of Patent: Feb. 16, 2021

(54) FOUL-RESISTANT COATING OF WINDOWS FOR OPTICAL PARTICLE SENSING

(71) Applicant: HONEYWELL INTERNATIONAL INC., Morris Plains, NJ (US)

(72) Inventors: Tobias Nebel, North Vancouver (CA); Markku Kellomaki, Pohjois-Savo (FI); Brendon Lyons, Monroe Township, NJ (US); Meghan Elizabeth Charochak, Elgin, IL (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 16/547,103

(22) Filed: Aug. 21, 2019

(65) Prior Publication Data

US 2020/0088624 A1   Mar. 19, 2020

Related U.S. Application Data

(60) Provisional application No. 62/732,332, filed on Sep. 17, 2018.

(51) Int. Cl.
| | | |
|---|---|---|
| *G01N 21/00* | (2006.01) | |
| *G01N 15/14* | (2006.01) | |
| *G01N 15/06* | (2006.01) | |
| *G01N 33/28* | (2006.01) | |
| *G01N 15/10* | (2006.01) | |

(52) U.S. Cl.
CPC ......... *G01N 15/1434* (2013.01); *G01N 15/06* (2013.01); *G01N 15/10* (2013.01); *G01N 33/28* (2013.01); *G01N 2015/0693* (2013.01)

(58) Field of Classification Search
CPC .... G01N 15/1434; G01N 15/06; G01N 15/10; G01N 15/1484; G01N 2015/0693; G01N 33/28; G01N 33/343; G01N 21/6486; G01N 21/643; G01N 21/6458; G01N 21/658; G01N 21/85; G01N 21/65; G01N 21/9501; G01N 21/6428; G01N 21/8806; G01N 21/94; G01N 21/53
USPC ............. 356/335–343, 73; 422/82.05, 82.08; 436/172
See application file for complete search history.

(56) References Cited

U.S. PATENT DOCUMENTS

| 4,902,137 A * | 2/1990 | Krieg ................. G01N 21/9027 250/223 B |
|---|---|---|
| 6,628,388 B2 * | 9/2003 | Darrow ................. G01N 21/05 356/336 |

(Continued)

*Primary Examiner* — Hoa Q Pham
(74) *Attorney, Agent, or Firm* — Jetter & Associates, P.A.

(57) ABSTRACT

A system for in-situ monitoring of particles in a process fluid includes a flow channel having a window for flowing the process fluid therethrough. The window includes an inner surface having a coating thereon that reduces a buildup rate of the particles on the inner surface. A light source is for directing a polarized beam along a first beam path through the window into the process fluid such that an output beam emerges from the process fluid along a second beam path. A polarizing filter positioned in the second beam path is for filtering the output beam. A photodetector is for detecting the output beam after passing the polarizing filter that generates signals that represent images of the particles in the process fluid. A controller coupled to the photodetector is for analyzing the signals to determine at least one parameter related to the particles in the process fluid.

20 Claims, 5 Drawing Sheets

(56) References Cited

U.S. PATENT DOCUMENTS

| | | | |
|---|---|---|---|
| 6,888,631 B2* | 5/2005 | Eriksson | G01N 15/0227 356/335 |
| 7,030,981 B2* | 4/2006 | Bishop | G01N 21/211 356/365 |
| 8,345,239 B1* | 1/2013 | Sieracki | G01N 21/23 356/365 |
| 9,902,911 B1 | 2/2018 | Kellomaki | |
| 10,072,219 B2* | 9/2018 | Kellomaki | G01N 15/06 |
| 2009/0056897 A1* | 3/2009 | Shevchenko | G01N 29/022 162/198 |
| 2010/0020168 A1* | 1/2010 | Ye | G01N 21/23 348/92 |
| 2012/0258547 A1* | 10/2012 | Von Drasek | G01N 21/6486 436/172 |
| 2013/0258336 A1* | 10/2013 | Ostermeyer | G01N 21/90 356/364 |
| 2014/0022547 A1* | 1/2014 | Knox | G01S 17/87 356/338 |
| 2015/0069247 A1* | 3/2015 | Asundi | G01N 21/23 250/341.3 |
| 2018/0304293 A1* | 10/2018 | Orla-Jensen | B05B 12/082 |
| 2019/0137932 A1* | 5/2019 | Ozcan | G03H 1/0005 |

\* cited by examiner

EXAMPLE COATINGS

| | TYPE | MANUFACTURER |
|---|---|---|
| 1 | SILCOKLEAN 1000 (ANTI-COKE) CVD OF SI, OTHERS | SILCOTEK |
| 2 | DURSAN (ANTI-STICK) CHEMICAL VAPOR DEPOSITION OF AMORPHOUS SI, C, O | SILCOTEK |
| 3 | AU-PLATING (HARD GOLD >0.0005") | SHARRETTS PLATING COMPANY |
| 4 | PC 915 D | GREYWALL COATINGS INC. |
| 5 | 900-SERIES | GREYWALL COATINGS INC. |
| 6 | TEFLON-BASED | GREYWALL COATINGS INC. |
| 7 | DIAMOND-LIKE CARBON CHEMICAL VAPOR DEPOSITION | IBC COATINGS |
| 8 | DIAMOND-LIKE CARBON PHYSICAL VAPOR DEPOSITION | IBC COATINGS |
| 9 | ALUMINIZING | IBC COATINGS |
| 10 | ANTI-FOULING TREATMENT 1 HYDROPHOBIC/OLEOPHOBIC | ACULON |
| 11 | ANTI-FOULING TREATMENT 2 HYDROPHILIC | ACULON |

DAY 9

FIG. 4D

COATED WINDOW

DAY 0

FIG. 4C

FOUL-RESISTANT COATING OF WINDOWS FOR OPTICAL PARTICLE SENSING

CROSS REFERENCE TO RELATED APPLICATIONS

This application claims the benefit of Provisional Application Ser. No. 62/732,332 entitled "FOUL-RESISTANT COATING OF WINDOWS FOR OPTICAL PARTICLE SENSING", filed Sep. 17, 2018, which is herein incorporated by reference in its entirety.

FIELD

Disclosed embodiments relate to sensors and methods for detecting the presence of particles in a liquid, and beam illumination for on-line imaging of the particles.

BACKGROUND

In some industrial applications, an on-line method is needed for monitoring particles in a moving fluid, such as the volume fraction and size distribution of particles in the liquid. The fluid generally comprises a liquid which can be highly viscous material at room temperature that flows slowly. For example, particles entrained in a heavy oil can detrimentally affect transportation and conversion processes if they agglomerate into deposits which can plug pipes and vessels.

In heavy oil upgrading, heavier materials are converted to lighter fractions and most of the sulfur, nitrogen and metals in the fluid need to be removed. Heavy oils include materials such as petroleum crude oil, atmospheric tower bottoms products, vacuum tower bottoms products, heavy cycle oils, shale oils, coal derived liquids, crude oil residuum, topped crude oils, and heavy bituminous oils extracted from oil sands. Most residual oil feedstocks to be upgraded contain some level of asphaltenes which are typically understood to be heptane insoluble compounds. Asphaltenes are relatively high molecular weight compounds containing heteroatoms which impart polarity.

Heavy oil is upgraded in a primary upgrading unit before it can be further processed into useable products. Primary upgrading units known in the art include coking processes, such as delayed or fluidized coking, and hydrogen addition processes such as ebullated bed or slurry hydrocracking (SHC). In SHC, a three-phase mixture of heavy liquid oil feed cracks in the presence of gaseous hydrogen over solid catalyst to produce lighter products under pressure at an elevated temperature. During an SHC reaction, it is important to minimize coking. Under certain process conditions, the asphaltenes can self-associate, or flocculate to form larger molecules, generally what is referred to as a mesophase, and precipitate out of solution to form coke. Mesophase is a semi-crystalline carbonaceous material defined as round, anisotropic particles. The presence of mesophase can serve as a warning that operating conditions are too severe in the SHC reactor, and that coke formation is likely to occur under prevailing condition.

The formation of mesophase particles is conventionally monitored by labor-intensive laboratory analysis that entail several hours of delay to actual process events. U.S. Pat. No. 9,902,911 to Kellomaki assigned to Honeywell International, the same assignee as for this application, provides a new method for on-line imaging of mesophase particles in oil for monitoring the volume fraction and size distribution of mesophase particles. Images are acquired with a polarized light imaging system which are then analyzed to identify the volume fraction and size distribution of the particles in the oil.

SUMMARY

This Summary is provided to introduce a brief selection of disclosed concepts in a simplified form that are further described below in the Detailed Description including the drawings provided. This Summary is not intended to limit the claimed subject matter's scope.

Disclosed embodiments recognize when imaging to determine particles in a flowing process fluid, known as fluid stream, such as using a polarized light imaging technique that utilizes a light beam transmitted through an optically transparent window, thereafter a "window", particles and fouling on the surface of the window build up over time that generally appear as white spots on a black background in the image provided by the imager (e.g., a photodetector such as a camera). Such white spots can falsely indicate the presence of particles in the fluid because the default image color is generally black.

Disclosed aspects solve this problem by coating the optically transparent window with a coating material that reduces a buildup rate of the particles on the surface of the window. In the case the process stream is an oil, such as a heavy oil, and the particles comprises a carbonaceous material such as mesophase particles, an oleophobic coating can be used on the surface of the window that can be covalently bonded to the surface of the window. An "oleophobic" coating material comprises a material that lacks an affinity to oils. Although the process stream is generally described comprising a reactor stream, disclosed aspects generally apply to any process stream, not just a reactor stream, but also a Hot High-Pressure Separator (HHPS) stream or a Hot Low-Pressure Separator (HLPS) stream, as well as other process streams.

DETAILED DESCRIPTION

Disclosed embodiments are described with reference to the attached figures, wherein like reference numerals are used throughout the figures to designate similar or equivalent elements. The figures are not drawn to scale and they are provided merely to illustrate certain disclosed aspects. Several disclosed aspects are described below with reference to example applications for illustration. It should be understood that numerous specific details, relationships, and methods are set forth to provide a full understanding of the disclosed embodiments.

For the imaging heavy oil, particles entrained in heavy oil fluid can detrimentally affect transportation and conversion processes if they agglomerate into deposits which can plug pipes and vessels. Some vacuum residue hydrocracking processes yield a specific type of carbon-based particle called mesophase, formed as a byproduct of heavy oil conversion. Particles, including mesophase, can be measured by visible light imaging, both in the laboratory and from on-line process sensors.

Some particles, such as mesophase particles, raise risks for imaging heavy oil. Heavy oil, such as vacuum residue, is dark colored (i.e. optically dense), limiting the passage of visible light through the fluid. As such, particle imaging in heavy oil is not practiced commercially. More significantly, on-line process sensor imaging of heavy oil generally requires an optically transparent window to transmit light into the fluid, and to seal the pressurized fluid into the pipe. Direct contact between heavy oil and the window results in the deposition of hydrocarbon and particulate residue on the window, which is called fouling. This foulant blocks the transmission of light into the fluid, thereby preventing the acquisition of images of particles in the fluid that disclosed aspects solve by adding a coating over the window.

Figure 1A:
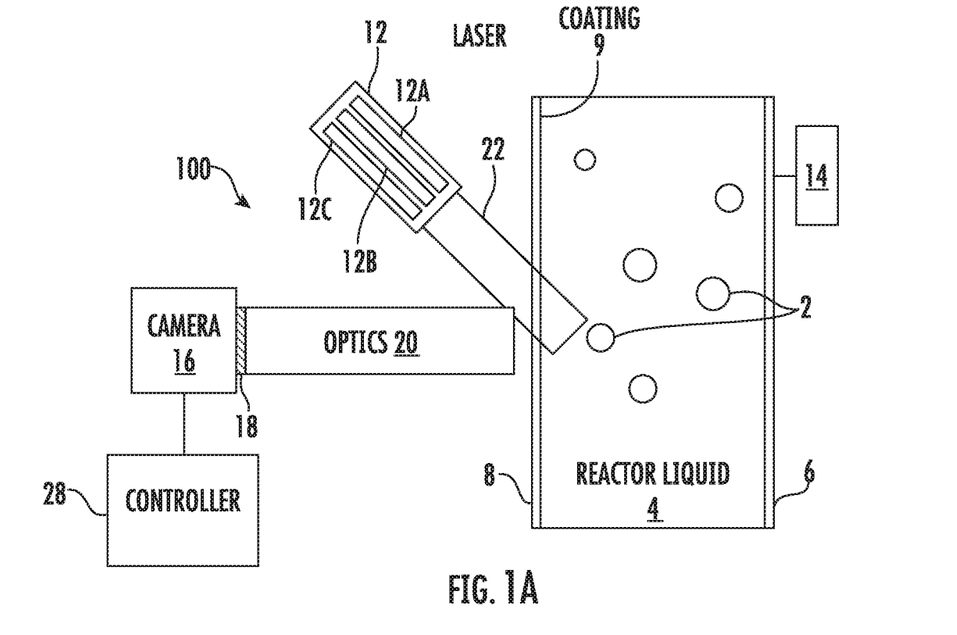
FIG. 1A shows an example on-line reflection-based imaging system using linear-polarized light that is obliquely (directional) reflected which can benefit from disclosed coating on the window of a flow channel with a coating material that reduces a buildup rate of the particles on the window, according to an example embodiment.

FIG. 1A shows an example on-line transmission-based imaging system 100 using linear-polarized light that is obliquely (directional) which can benefit from a disclosed coating 9 of the window 8 with a coating material that reduces a buildup rate of the particles on the window 8. The window 8, comprises an optically transparent material, such as quartz. System 100 can be used for the in-situ monitoring of mesophase particles 2 that may be present in a moving process liquid that is flowing through a flow channel 4 which includes a window 8 that has a disclosed coating 9 thereon on its inside surface that can be part of (integrated with) the channel wall 6. The window 8 which can be a part of side-stream from a reactor chamber with known cross-sectional dimensions at the area where the light beam 22 through the window 8 illuminates a target area in the reactor liquid.

A side-stream from a process chamber such as a reactor chamber can for example comprise a 12" (inch)diameter pipe leaving a reactor, where a slip stream of that is taken (e.g., ~½" diameter pipe) which is sent to the flow channel for analysis by the online sensor. The side or slip stream provides a smaller volume of material drawn for analysis and is then either discarded or returned to the main volume. This is done so that the fluid's pressure, temperature and volume can be changed to be within limits for the flow channel and analysis.

The channel wall 6 can comprise 316 stainless steel, although generally any metal that is compatible with the process conditions can be used. The window 8 is secured such that all the piping and vessels hold pressure and thus do not leak. It is possible that a sight glass can be used on the reactor vessel or any process line/vessel itself and the imaging performed using that. The flow rate through the side-stream can be measured by a flow sensor 14. Thus, the volumetric flow rate through the channel 4 can be calculated. Window 8 comprises an optically transmissive material such as glass or sapphire, which is transparent to the wavelength of light from the light source shown by example as a laser 12.

For linear-polarized light imaging, a laser 12 directs a light beam 22 through the window 8 and into channel 4. The laser 12 can comprise a pulsed laser or a continuous laser. The laser 12 shown in FIG. 1A combines the output of a plurality of laser diode bars 12A, 12B, 12C, by spatial multiplexing to become substantially parallel with an optical axis, while individually rotating the polarization of each laser diode output so that the combined output has substantially a single (linear) polarization. Each laser diode bar 12A, 12B, 12C shown comprises one or more diode lasers. An example laser illuminator configured with a plurality of laser diode bars is described in U.S. Pat. No. 7,817,693 to Alahautala et al, which is incorporated herein by reference for its laser illuminator. A suitable laser illuminator is commercially available as the Cavilux Smart model from Cavitar Oy (Valkeakoski, FI). However, disclosed light sources besides lasers can generally be any other incoherent light source.

The light source(s) being pulsed generally increases the lifetime of the light source(s). The light source(s) can itself provide polarized light, or the light source can provide non-polarized light that is then polarized by a polarizing filter. The laser 12 can be replaced by a halogen-based light source or by light emitting diodes (LEDs). However, a laser 12 when embodied as a laser diode generally provides a higher intensity of illumination compared to these other types of light sources. The light beam 22 may comprise pulsed laser beam which may have a pulse duration of about 10 ns to 10 µs. The pulse duration used generally depends on image resolution of the photodetector shown as a camera 16 that comprises a photodetector array that is used and the mesophase velocity of the process fluid in channel 4 that is adjacent to the window 8. A controller 28 is coupled to the camera 16 for analyzing the photodetector signals generated by the camera to determine at least one parameter related to the particles in the process fluid flowing in the channel 4, such as a volume fraction or a size distribution of mesophase particles.

For example, if one pixel movement of the process liquid or fluid is permitted for the camera 16, which results in acceptable blur, the pulse duration may be set by $\Delta T \ll L_P/|V_M|$ where $L_P$ is the pixel size in µm and $V_M$ is the mesophase velocity near the window in µm/µs. The mesophase velocity has two components: $V_M = V_L + V_V$ where $V_L$ is the velocity of the process fluid in the channel and $V_V$ is the relative vibration velocity between the camera 16 and the channel 4. The mesophase movement is a combination of flow velocity and vibration of the channel 4. In this example, the pulse duration of the light beam is generally short enough to allow movement of mesophase particles for up to one pixel during the exposure.

Since the light beam 22 emitted from the laser 12 is typically substantially linearly polarized, no polarization filter is used on the illumination side. However, a "clean up" polarization filter can be positioned in front of the laser 12 if desired to generate a light beam 22 that is essentially completely linearly polarized. Even without a "clean up"

polarization filter, the light beam 22 from laser diodes source as the laser 12 will typically be over 90% linearly polarized. The presence of a polarization filter only slightly reduces the intensity as the laser 12 may already be substantially linearly polarized.

Output light that is backscattered or reflected by the mesophase particles 2 is collected by imaging optics 20, and a polarizing filter 18 that filters or blocks the component of this backscattered light which has a polarization state parallel to that of the incident light beam 22. The incident light beam 22 can illuminate a target area in the process liquid in the channel 4 that typically ranges from about 20 to 25 mm$^2$. The size of the illuminated target area is sufficient to permit rapid and accurate detection of the mesophase particles. For a circular target area, the diameter can be about 5 mm, or for a square target area each side can be about 5 mm.

The camera 16 or other photodetector can image only the component with the polarization state perpendicular to that of the light beam 22. Some of the particles that reflect light may not be mesophase particles, and some may only be partially mesophasic. Since the dimensions of the channel 4 are known and the flow rate through the channel 4 can be measured, the volume fraction of mesophase particles flowing through channel 4 can be calculated by determining the size of the mesophase particles that are detected. The size distribution of mesophase particles flowing through channel 4 can be determined by comparing the images to calibration data measured with mesophase particles of known sizes.

The camera 16 or other photodetector and laser 12 are configured so that the image scale is sufficient to allow individual mesophase particles in the process liquid to be discerned. Thus, the photodetectors shown as a camera 16, should generally be coupled with imaging optics 20 which results in a pixel size (the size of target area projected on a single pixel of the detector array) that does not exceed one quarter of the typical width of mesophase particles. This corresponds to about 0.1 to 5.0 microns per pixel in the image when using adequate lenses. Conventional lens can be employed as the imaging optics 20 with the camera 16 when the process liquid and mesophase particles are moving in a relatively constant rate. However, if the process liquid flow pattern is turbulent, a telecentric lens system that provides a relatively large depth of field can be used so that fluctuations in the movements in the process liquid relative to the camera 16 does not change the image size.

The short exposure time created by the light beam 22 when it is a pulsed beam allows the camera 16 or other photodetector, with correspondingly short integration times, to obtain good images of the target area in the process liquid by reducing or eliminating the adverse effects caused by motion-blurring in the direction of movement of the process liquid. In the case the camera 16 comprises a charge-coupled device (CCD), a short integration time enables its pixels to collect less light and a longer integration time enables pixels to collect more light. The higher illumination intensity provided by a laser 12 is advantageous as more light means a higher signal to noise ratio. A complementary metal-oxide-semiconductor (CMOS) array-based photodetector as the camera 16 can also be employed.

Figure 1B:
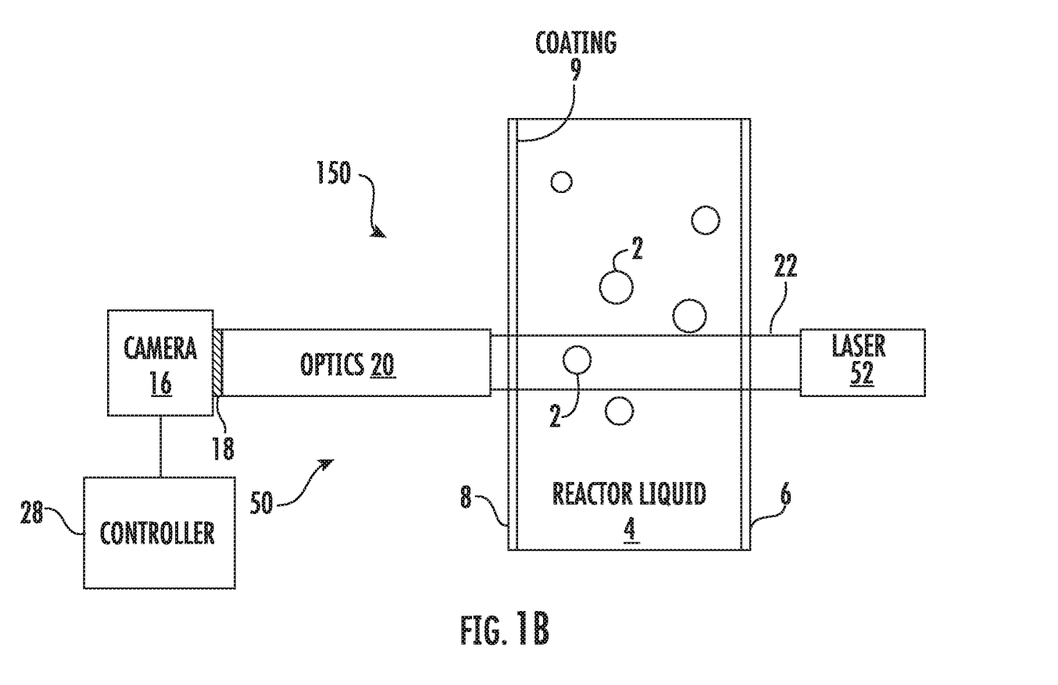
FIG. 1B shows an example on-line transmission-based imaging system using linear-polarized light that can benefit from disclosed coating on the window of a flow channel with a coating material that reduces a buildup rate of the particles on the window, according to an example embodiment.

FIG. 1B illustrates a linear-polarizing transmission-based light imaging system 150 for in-situ monitoring of mesophase particles 2 that are present in a moving process liquid that is flowing through channel 4 which is defined by window 8 that has a disclosed coating 9 thereon. The window 8 or windows as noted above can be a part of a side-stream from a process reactor chamber with known cross-sectional dimensions at the area where the light beam 22 illuminates a target area in the process liquid. A laser 52 directs a pulsed laser beam 22 through window 8 and into channel 4. The laser 52 can be the same as the laser 12 shown in FIG. 1A. No polarization filter is generally needed on the illumination side, but a "clean up" polarization filter can be positioned in front of the laser 52 if desired.

Output light that interacts with mesophase particles 2 is collected by imaging optics 20 and polarizing filter 18 filters or blocks the component of this backscattered light which has a polarization state parallel to that of the laser beam 22. The camera 16 images only the component with the polarization state perpendicular to that of the laser beam 22.

A circularly polarized light source can also be employed to detect the presence of mesophase particles. In particular, linearly polarized light can be converted into circularly polarized light with a quarter-wave plate. In this case circularly polarized light interacts with the birefringent mesophase particles and the transmitted or reflected light is then analyzed.

Figure 2:
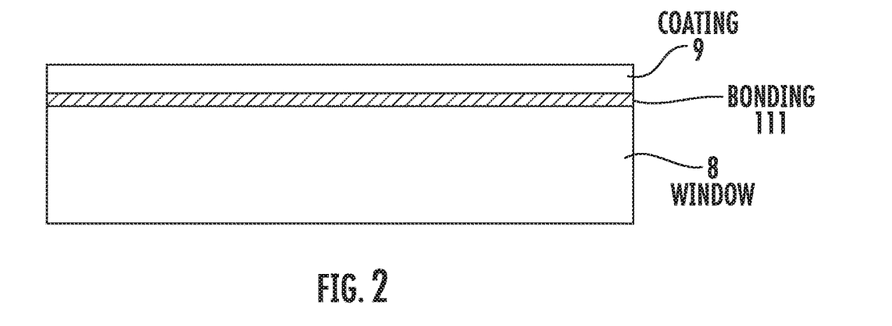
FIG. 2 is a cross-sectional depiction of an example coating on the window of a flow channel comprising an oleophobic coating material that forms a bond with the substrate material of the window such as a glass window, according to an example embodiment.

FIG. 2 is a cross-sectional depiction of an example coating 9 on the window 8 of a flow channel that can comprise an oleophobic coating that forms a bond shown as bonding 111 with a substrate material for the window 8, such as comprising a glass. The bonding 111 can be a chemical (i.e., covalent) bond formed by one particular coating 9 termed self-assembled monolayer of phosphonates (SAMP) which can provide a hydrophobic surface, such as a super-hydrophobic surface. A hydrophobic surface is a surface that has a contact angle for water greater than 90°, while a superhydrophobic surface provides a water contact angle >150°. Aculon, Inc. provides SAMP materials commercially.

A monolayer is known to be a nanoscale coating that is one molecule thick that is generally 1 to 4 nms thick. A phosphonate is a phosphorous acid that combines a reactive phosphonic acid or "reactive head group" and a carbon-based tail group connected through a phosphorous carbon bond (P—C). The reactive "heads" react with the surface of the oxygen atoms on the surface of the window 8 through relatively strong, stable metal phosphorous bonds, and the tails stick out from the surface can be chosen for their chemical functionality (hydrophobic, oleophobic, non-stick, adhesion promotion, etc.).

Disclosed embodiments can be generally applied to particle measurement in any process fluid that generally comprises a liquid. For example, disclosed imaging besides for hydrocracking processing, can be used for pipeline transportation of crude oil, heat exchangers (crude oil distillation, visbreaking), and fuel-fired furnaces for delayed coking.

EXAMPLES

Disclosed embodiments are further illustrated by the following specific Examples, which should not be construed as limiting the scope or content of this Disclosure in any way.

Figure 3:
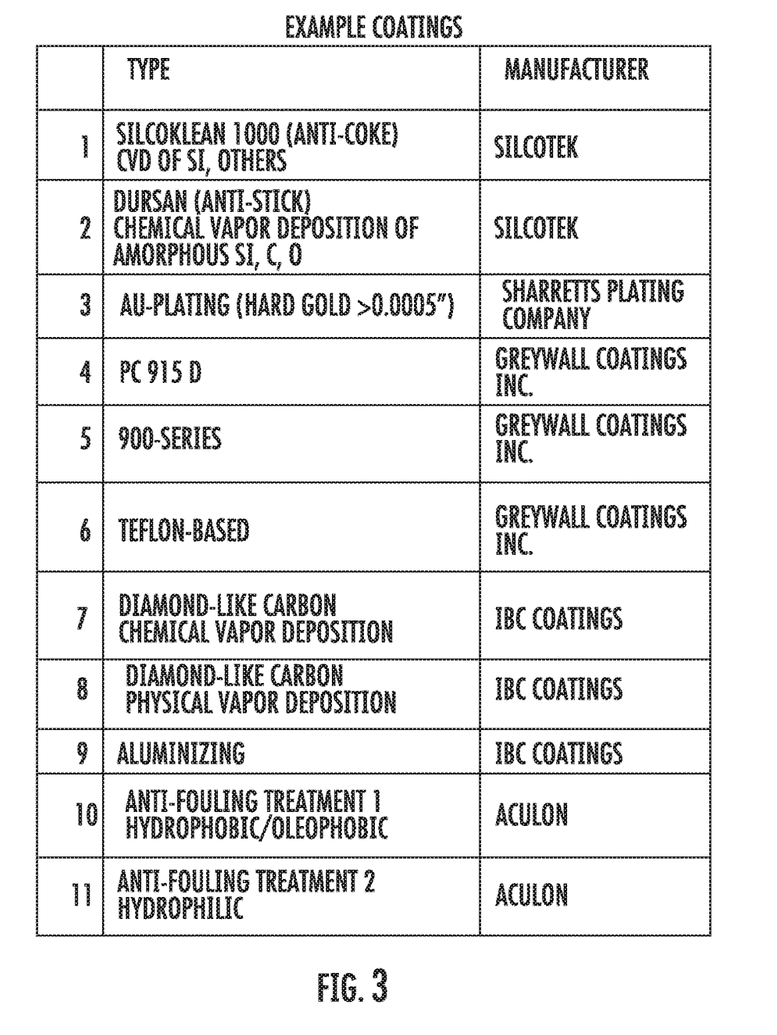
FIG. 3 shows some example coating materials that can be used for coating the window of a flow channel.

FIG. 3 shows some example coating materials that can be used for coating the window of a flow channel. The coatings shown are commercially available and include some metal materials as well as some non-metal materials.

Figure 4A:
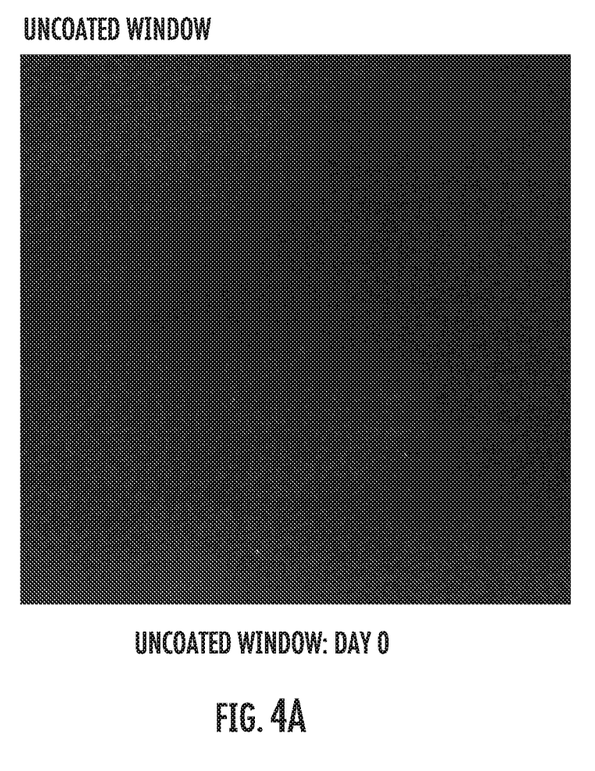
FIG. 4A is a scanned image showing an uncoated window at day 0.
Figure 4B:
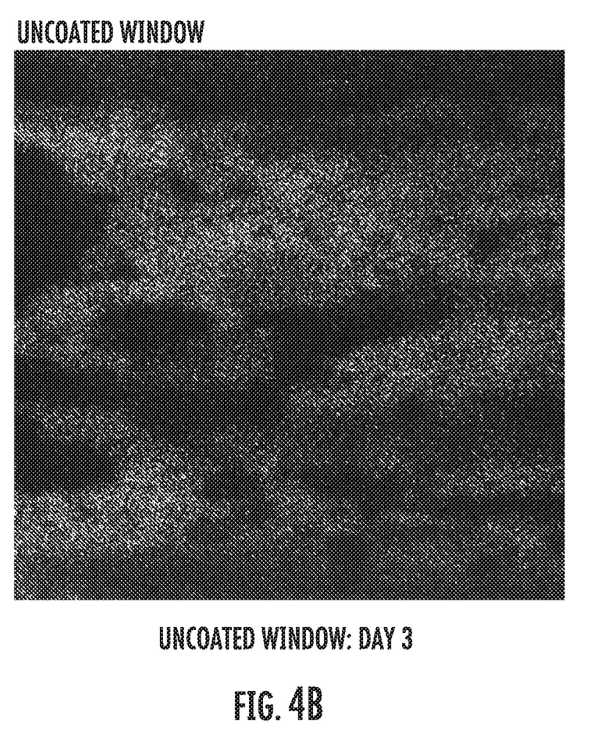
FIG. 4B is a scanned image of the uncoated window at day 3 having a large number of white spots that indicate significant surface fouling.

FIG. 4A is a scanned image showing an uncoated window at day 0, and FIG. 4B is a scanned image of the uncoated window at day 3 having a large number of white spots that indicate significant window surface fouling.

Figure 4C:
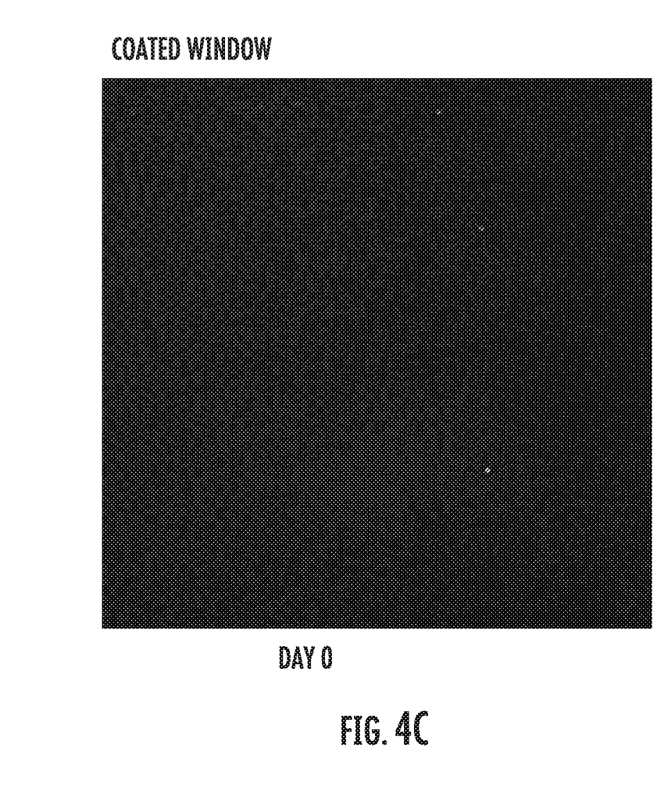
FIG. 4C is a scanned image showing a disclosed window coated with a self-assembled monolayer of phosphonates at day 0.
Figure 4D:
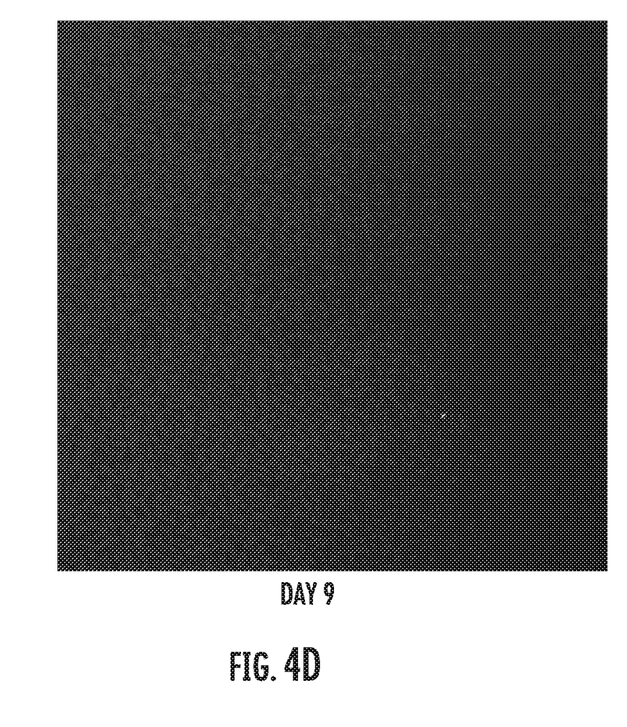
FIG. 4D is a scanned image showing a disclosed window coated with the self-assembled monolayer of phosphonates at day 9 lacking any noticeable white spots which evidences essentially no fouling.

FIG. 4C is a scanned image showing a disclosed window coated with a self-assembled monolayer of phosphonates coating at day 0, and FIG. 4D is a scanned image showing the window coated with the self-assembled monolayer of phosphonates coating at day 9 lacking any noticeable white spots that evidences essentially no fouling of the window surface.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

The invention claimed is:

1. A system for in-situ monitoring of particles in a process fluid, comprising:
   a flow channel comprising a window for flowing the process fluid therethrough, wherein the process fluid includes birefringent particles, and wherein an inner surface of the window includes a coating that reduces a buildup rate of the particles on the inner surface;
   a light source for directing a polarized beam having a first polarization state along a first beam path into the process fluid such that the polarized beam interacts with the birefringent particles so that along a first beam path into the process fluid such that an output beam having a changed polarization state relative to the first polarization state emerges from the process fluid along a second beam path;
   a polarizing filter positioned in the second beam path configured to transmit the changed polarization state of the output beam and to block another portion of the output beam that is backscattered from the birefringent particles and has a polarization state parallel to the first polarization state;
   a photodetector for detecting the changed polarization state of the output beam after passing the polarizing filter that generates signals which represent images of the birefringent particles in the process fluid, and
   a controller coupled to the photodetector for analyzing the signals to determine at least one parameter related to the birefringent particles in the process fluid.

2. The system of claim 1, wherein the birefringent particles comprise mesophase particles, and wherein the parameter comprises a volume fraction or a size distribution of the mesophase particles.

3. The system of claim 1, wherein the light source comprises a laser diode light source, and wherein the polarized beam comprises linearly polarized light or circularly polarized light.

4. The system of claim 1, wherein the process fluid comprises an oil, wherein the window comprises a glass, and wherein the coating comprises a monolayer oleophobic coating that is covalently bonded to the inner surface.

5. The system of claim 1, wherein the light source comprises a polarized light source.

6. The system of claim 1, wherein the polarized beam comprises a linearly polarized beam.

7. The system of claim 1, wherein the polarized beam comprises a pulsed beam.

8. The system of claim 1, wherein the process fluid comprises a reactor fluid.

9. A method of in-situ monitoring a process fluid, comprising:
   flowing the process fluid through a flow channel comprising a window, wherein the process fluid includes birefringent particles, and wherein an inner surface of the window includes a coating that reduces a buildup rate of the birefringent particles on the inner surface;
   directing a polarized beam having a first polarization state along a first beam path in through the window into the process fluid such that an output beam having a changed polarization state relative to the first polarization state emerges from the process fluid out through the window along a second beam path;
   polarizing filtering comprising transmitting the changed polarization state of the output beam and blocking another portion of the output beam that is backscattered from the birefringent particles and has a polarization state parallel to the first polarization state;
   detecting the changed polarization state of the output beam after passing the polarizing filtering to generate signals that represent images of the birefringent particles in the process fluid, and
   analyzing the signals to determine at least one parameter related to the birefringent particles.

10. The method of claim 9, wherein the process fluid comprises an oil, and wherein the birefringent particles are formed in a hydrocarbon conversion reactor.

11. The method of claim 10, wherein the polarized beam is provided by a polarized light source.

12. The method of claim 9, wherein the polarized beam is reflected from a target area in the process fluid to form the output beam.

13. The method of claim 9, wherein the polarized beam is transmitted from a target area in the process fluid to form the output beam.

14. The method of claim 9, wherein the window comprises a glass, and wherein the coating comprises a monolayer oleophobic coating that is covalently bonded to the inner surface.

15. The method of claim 9, wherein the polarized beam comprises a linearly polarized beam.

16. The method of claim 9, wherein the polarized beam comprises a pulsed beam.

17. The method of claim 9, wherein the birefringent particles comprise mesophase particles, and wherein the parameter comprises a volume fraction or a size distribution of the mesophase particles.

18. A system for in-situ monitoring of particles in a process fluid, comprising:
   a flow channel comprising a window for flowing the process fluid therethrough, wherein the process fluid includes birefringent particles, and wherein an inner surface of the window includes a coating that reduces a buildup rate of the particles on the inner surface, wherein the process fluid comprises an oil, wherein the window comprises a glass, and wherein the coating comprises a monolayer oleophobic coating that is covalently bonded to the inner surface;
   a light source for directing a polarized beam having a first polarization state along a first beam path into the process fluid such that the polarized beam interacts with the birefringent particles so that along a first beam path into the process fluid such that an output beam having a changed polarization state relative to the first polarization state emerges from the process fluid along a second beam path;
   a polarizing filter positioned in the second beam path configured to transmit the changed polarization state of the output beam and to block another portion of the output beam that is backscattered from the birefringent particles and has a polarization state parallel to the first polarization state;

a photodetector for detecting the changed polarization state of the output beam after passing the polarizing filter that generates signals which represent images of the birefringent particles in the process fluid, and a controller coupled to the photodetector for analyzing the signals to determine at least one parameter related to the birefringent particles in the process fluid.

19. The system of claim 18, wherein the birefringent particles comprise mesophase particles, and wherein the parameter comprises a volume fraction or a size distribution of the mesophase particles.

20. The system of claim 18, wherein the light source comprises a laser diode light source, and wherein the polarized beam comprises linearly polarized light or circularly polarized light.

* * * * *